United States Patent [19]
Chen et al.

[11] Patent Number: 6,063,958
[45] Date of Patent: May 16, 2000

[54] METHOD OF RECOVERING ADIPIC ACID AND 6-HYDROXYCAPROIC ACID FROM WASTE SOLUTION OF ALKALI METAL SALTS OF ORGANIC ACIDS COMING FROM THE PROCESS OF CYCLOHEXANE OXIDATION

[75] Inventors: Kuang-Ruei Chen; Jih-Dar Hwang; Shu-Hui Chen, all of Kaohsiung, Taiwan

[73] Assignee: China Petrochemical Development Corporation, Taipei, Taiwan

[21] Appl. No.: 09/218,613

[22] Filed: Dec. 22, 1998

[51] Int. Cl.$^7$ .............................. C07C 51/42; C07C 51/48
[52] U.S. Cl. ......................... 562/580; 562/593; 562/543
[58] Field of Search ..................................... 562/580, 593, 562/543

[56] References Cited

U.S. PATENT DOCUMENTS

| | | |
|---|---|---|
| 3,524,892 | 8/1970 | Horlenko et al. . |
| 3,859,335 | 1/1975 | Schindlbauer et al. .............. 260/484 R |
| 4,052,441 | 10/1977 | Brunner ..................................... 560/17 |
| 5,900,506 | 5/1999 | Fache et al. ............................. 562/593 |

FOREIGN PATENT DOCUMENTS

| | | |
|---|---|---|
| 1206417 | 12/1963 | Germany . |
| 53-33567 | 9/1978 | Japan . |

*Primary Examiner*—Rosalynd Keys
*Attorney, Agent, or Firm*—Clifford W. Browning; Woodard, Emhardt, Naughton, Moriarty & McNett, Patent and Trademark Attorneys

[57] ABSTRACT

A method of recovering adipic acid and 6-hydroxycaproic acid from the waste solution of alkali metal salts of organic acids coming from the process of cyclohexane oxidation, which comprises:

(i) basifying the reaction mixture coming from cyclohexane oxidation with an aqueous solution of an alkali-metal base so that the organic acids essentially comprising adipic acid and 6-hydroxycaproic acid therein, are saponified, extracting the formed alkali metal salts of organic acids from the mixture with water, then acidifying the aqueous extract comprising the alkali metal salts of organic acids to a pH value of 3 or lower with an aqueous solution of a protic inorganic acid, as a result, said aqueous extract is separated into an oily layer and an aqueous layer;

(ii) extracting the organic acid from said oily layer obtained from the step (i) with an aqueous solution of a protic inorganic acid, to obtain an aqueous extract;

(iii) extracting the organic acid from the aqueous layer obtained from the step (i) with an organic solvent selected from alcohols, ketones, esters or the mixtures thereof, to obtain an oily extract;

(iv) extracting the organic acid from the aqueous extract obtained from the step (ii) with an organic solvent selected from alcohols, ketones, esters or mixtures thereof, to obtain an oily extract; and (v) combining and distilling the oily extracts obtained from the steps (iii) and (iv), to recover the organic acid essentially comprising adipic acid and 6-hydroxycaproic acid.

15 Claims, 3 Drawing Sheets

METHOD OF RECOVERING ADIPIC ACID AND 6-HYDROXYCAPROIC ACID FROM WASTE SOLUTION OF ALKALI METAL SALTS OF ORGANIC ACIDS COMING FROM THE PROCESS OF CYCLOHEXANE OXIDATION

FIELD OF THE INVENTION

The present invention relates to a method of recovering adipic acid and 6-hydroxycaproic acid from the waste solution of alkali metal salts of organic acids coming from the process of cyclohexane oxidation.

BACKGROUND OF THE INVENTION

Cyclohexanol and cyclohexanone, which are the main products of cyclohexane oxidation, are the important raw materials for producing adipic acid and caprolactam. Said oxidation is usually conducted by direct air oxidation (i.e. air is used as an oxidant) in a liquid phase in the presence of a catalyst. In the process of oxidation, a peroxide will form first and then will decompose into some neutral and acidic substances. The acid substances may form esters by reacting with neutral alcohols. Therefore, besides the main products (i.e. cyclohexanone and cyclohexanol), by-products such as dicarboxylic acids, monocarboxylic acids, oxycarboxylic acids and small amount of alcohols, aldehydes, esters and other organic matters with unknown composition also exist in the reaction mixture.

Among these by-products, adipic acid and 6-hydroxycaproic acid have high economic values because they can be converted, by esternfication/hydrogenation, into 1,6-hexanediol, which is an important raw material for producing polyurethane resins and polyester resins.

There have been many patents disclosing the methods of recovering useful organic acids such as adipic acid and 6-hydroxycaproic acid from the reaction mixture of cyclohexane oxidation and converting them into 1,6-hexanediol. For example, JP-B-SHO 53-33567 discloses a method comprising the following steps: basifying the reaction mixture of cyclohexane oxidation with sodium hydroxide; separating the lower layer which is an alkaline solution of sodium salts of organic acids and acidifying it layer with sulfuric acid; separating the obtained oily layer comprising the organic acids from the aqueous layer comprising sodium sulfate; extracting the separated oily layer with an organic substance-free solution of sodium sulfate at a concentration of 15% by weight or higher; combining the obtained aqueous extract and the previously obtained aqueous layer comprising sodium sulfate and again extracting said combined solution with an organic solvent, distilling off the solvents in the organic extract, and utilizing the obtained residues to prepare 1,6-hexanediol through esterification/hydrogenation. Although the method of JP-B-SHO 53-33567 is superior to the methods as described in U.S. Pat. No. 3,524,892 and GP 1,206,417 wherein the substances useful for producing 1.6-hexanediol are recovered by directly extracting the reaction mixture of cyclohexane oxidation with water, it still has the following disadvantages:

1. As the oily layer comprising the organic acids is extracted by an aqueous solution of sodium sulfate, the efficacy for extracting the useful organic acids such as adipic acid and 6-hydroxycaproic acid is difficult to be raised.
2. After extraction by an aqueous solution of sodium sulfate, the waste oily layer, still has higher concentration of sodium ions. When said waste oily layer, alone or together with other fuel oils, is burned in a boiler or a combustion furnace, it will be apt to cause corrosion of the combustion equipment and consequently the lifetime of said equipment may be shortened.
3. The organic solvents for use in extracting the useful organic acids in the aqueous layer are not properly selected. Namely, said method does not use the organic solvents with higher extraction efficacy.
4. When the aqueous extract obtained by extracting the oily layer with the solution of sodium sulfate is combined with the aqueous layer separated from the alkaline solution of sodium salts of organic acids after acidification with sulfuric acid, the organic matters in the combined aqueous solution will increase. If lesser amount of organic solvents are used to extract said combined aqueous solution, the useful organic acids can not be effectively recovered and consequently the residual aqueous solution (also called mother liquor) will have a higher COD value. When the mother liquor is recycled for use, its COD value will increase rapidly. Therefore, upon formation of anhydrous sodium sulfate crystals by concentration, the equipment for concentration and crystallization as well as the quality of sodium sulfate crystals will be adversely affected. In contrast, if more amount of organic solvents are used for extraction, sodium sulfate crystals may be precipitated out and cause problems in handling the extract.

The present inventor made an effort to resolve the aforesaid disadvantages of the prior art and finally found the method according to the present invention as described below can achieve this purpose. Thus, the present invention has been completed.

OBJECT OF THE INVENTION

It is therefore an object of the present invention to provide a method of effectively recovering adipic acid and 6-hydroxycaproic acid from the waste solution of alkali metal salts of organic acids coming from the process of cyclohexane oxidation.

It is another object of the present invention to reduce the concentration of alkali metal ions in the waste oily layer obtained in the process of recovering adipic acid and 6-hydroxycaproic acid, so that said waste oily layer can be further utilized as a fuel for a boiler or a combustion system.

It is still another object of the present invention to improve the quality of alkali metal salts of inorganic acids by-produced in the process of recovering adipic acid and 6-hydroxycaproic acid.

SUMMARY OF THE INVENTION

The present invention relates to a method of recovering adipic acid and 6-hydroxycaproic acid from the waste solution of alkali metal salts of organic acids coming from the process of cyclohexane oxidation, which comprises:

(i) basifying the reaction mixture coming from cyclohexane oxidation with an aqueous solution of an alkali-metal base so that the organic acids essentially comprising adipic acid and 6-hydroxycaproic acid therein, are saponified, extracting the formed alkali metal salts of organic acids from the mixture with water, then acidifying the aqueous extract comprising the alkali metal salts of organic acids to a pH value of 3 or lower with an aqueous solution of a protic inorganic acid, as a result, said aqueous extract is separated into an oily layer and an aqueous layer;

(ii) extracting the organic acid from said oily layer obtained from the step(i) with an aqueous solution of a protic inorganic acid, to obtain an aqueous extract;

(iii) extracting the organic acid from said aqueous layer obtained from the step (i) with an organic solvent selected from alcohols, ketones, esters or the mixtures thereof, to obtain an oily extract;

(iv) extracting the organic acid from the aqueous extract obtained from the step(ii) with an organic solvent selected from alcohols, ketones, esters or mixtures thereof, to obtain an oily extract; and (v) combining and distilling the oily extracts obtained from the steps (iii) and (iv), to recover the organic acid essentially comprising adipic acid and 6-hydroxycaproic acid.

DESCRIPTION OF THE REFERENCE NUMERALS

Figure 1:
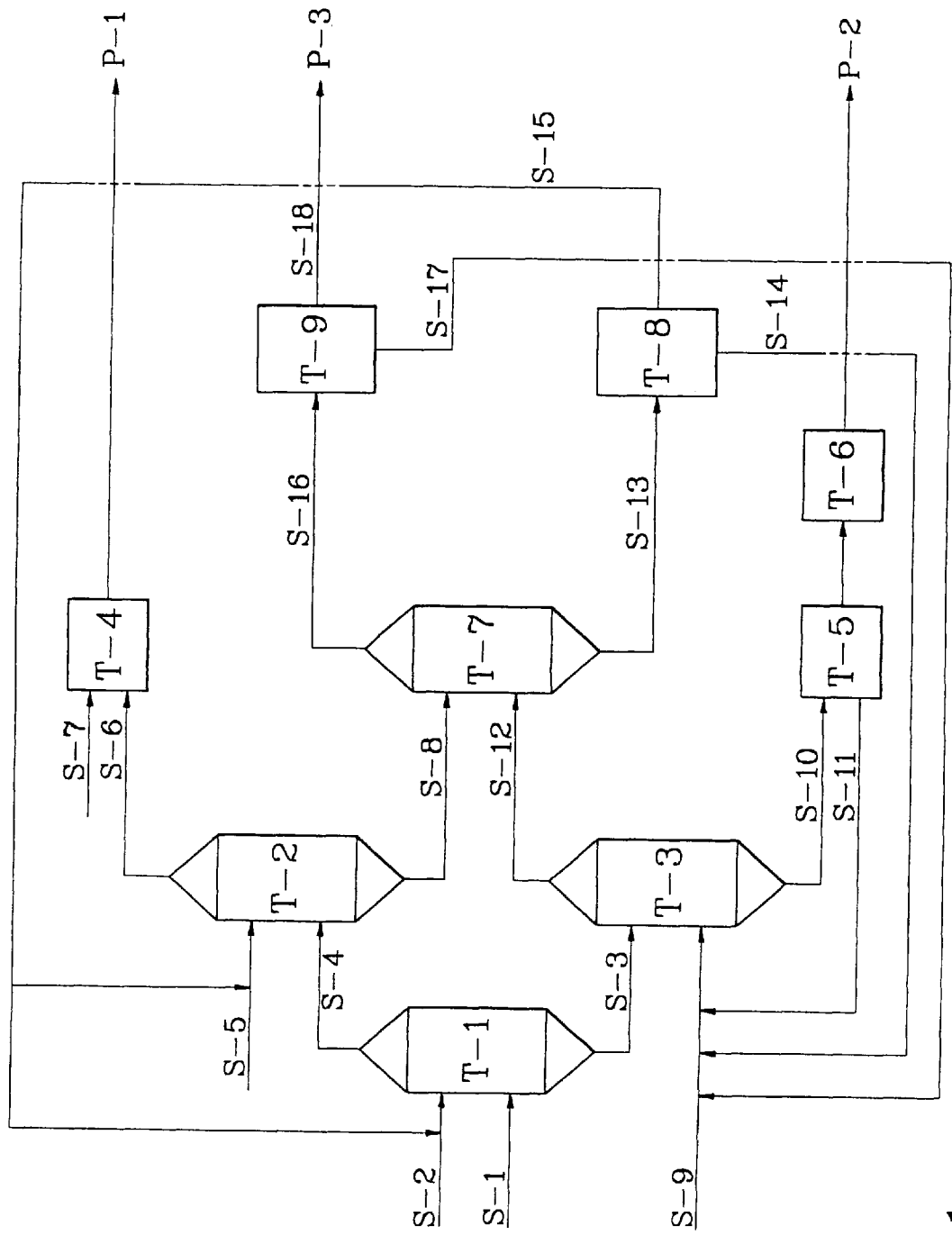
FIG. 1 is a flow chart of recovering adipic acid and 6-hydroxycaproic acid from the waste solution of the sodium salts of the organic acids coming from the process of cyclohexane oxidation in accordance with one preferred embodiment of the present invention.

| | |
|---|---|
| S-1 | an aqueous extract comprising the sodium salts of organic acids (a waste solution of sodium salts of organic acids) |
| S-2 | an aqueous solution of a protic inorganic acid |
| S-3 | an aqueous layer |
| S-4 | an oily layer |
| S-5 | an aqueous solution of a protic inorganic acid |
| S-6 | a waste oily layer |
| S-7 | a heavy oil (fuel oil) |
| S-8 | an aqueous extract comprising the organic acids dissolved in the protonreleasable inorganic acid) |
| S-9 | organic solvents |
| S-10 | residual aqueous layer comprising the sodium salt of inorganic acid |
| S-11 | recovered organic solvents |
| S-12 | an oily extract comprising the organic acids |
| S-13 | aqueous extract left after extracting S-8 with S-12 |
| S-14 | recovered organic solvents |
| S-15 | mother liquor comprising the protic inorganic acid |
| S-16 | an oily extract comprising the organic acids |
| S-17 | recovered organic solvents |
| S-18 | recovered adipic acid and 6-hydroxycaproic acid |
| T-1 | acidifying tank |
| T-2 | extracting tower |
| T-3 | extracting tower |
| T-4 | mixing tank |
| T-5 | stripping tower |
| T-6 | concentrating and crystallizing tank |
| T-7 | extracting tower |
| T-8 | stripping tower |
| T-9 | distilling tower |
| P-1 | fuel |
| P-2 | crystals of sodium salts of inorganic acids |
| P-3 | 1,6-hexanediol |

DETAILED DESCRIPTION OF THE INVENTION

The present invention relates to a method of recovering adipic acid and 6-hydroxycaproic acid from the waste solution of alkali metal salts of organic acids coming from the process of cyclohexane oxidation, which comprises:

(i) basifying the reaction mixture coming from cyclohexane oxidation with an aqueous solution of an alkali-metal base so that the organic acids essentially comprising adipic acid and 6-hydroxycaproic acid therein, are saponified, extracting the formed alkali metal salts of organic acids from the mixture with water, then acidifying the aqueous extract comprising the alkali metal salts of organic acids to a pH value of 3 or lower with an aqueous solution of a protic inorganic acid, as a result, said aqueous extract is separated into an oily layer and an aqueous layer;

(ii) extracting the organic acid from said oily layer obtained from the step(i) with an aqueous solution of a protic inorganic acid, to obtain an aqueous extract;

(iii) extracting the organic acid from the aqueous layer obtained from the step (i) with an organic solvent selected from alcohols, ketones, esters or the mixtures thereof, to obtain an oily extract;

(iv) extracting the organic acid from the aqueous extract obtained from the step(ii) with an organic solvent selected from alcohols, ketones, esters or mixtures thereof, to obtain an oily extract; and (v) combining and distilling the oily extracts obtained from the steps (iii) and (iv), to recover the organic acid essentially comprising adipic acid and 6-hydroxycaproic The term "organic acids" or "the useful organic acids" herein indicates the organic acids essentially comprising adipic acid and 6-hydroxy caproic acid. The term "a protic inorganic acid" herein is sometimes briefly called "an inorganic acid".

In the step (i) of the method according to the present invention, the reaction mixture coming from cyclohexane oxidation is basified with an aqueous solution of alkali metal base, for example, sodium hydroxide so that the organic acids essentially comprising adipic acid and 6-hydroxycaproic acid, therein are saponified. Then, the formed alkali metal salts of organic acids are extracted with water. The obtained aqueous extract (also called a waste solution of the alkali metal salts of organic acids) is further acidified to a pH value of 3 or lower with an aqueous solution of a protic inorganic acid, for example, sulfuric acid, phosphoric acid, nitric acid or hydrochloric acid. As a result, said aqueous extract is separated into an oily layer and an aqueous layer. Said oily layer and said aqueous layer are further treated in the following steps to recover the useful organic acids.

In the step (ii) of the method according to the present invention, the useful organic acids essentially comprising adipic acid and 6-hydroxycaproic acid, are extracted from the oily layer obtained from the step (i). The oily layer obtained from the step (i) usually contains 0.2 to 0.9% by weight of sodium ion in case that sodium hydroxide is used as a basifying and saponifying agent. If an aqueous solution of a salt having higher concentration of sodium ion (for example, an aqueous solution of sodium sulfate) is used to extract the oily layer, the waste oily layer after extraction will contain as high as 0.2 to 0.5% by weight of sodium ion. This high concentration of sodium ion will limit the use of said waste oil as a fuel for a boiler or a combustion furnace. Besides, the yield of the useful organic acids such as adipic acid and 6-hydroxycaproic acid can not be significantly raised through increasing the concentration of sodium ion in the extracting agent.

Based on the above reasons, instead of using the aforesaid aqueous solution of salts as the extracting agent, the present inventor uses an aqueous solution of a protic inorganic acid such as sulfuric acid, phosphoric acid, nitric acid or hydrochloric acid as the extracting agent. The concentration of the inorganic acids in the aqueous solution is usually 5 to 50% by weight, preferably 15 to 30% by weight. The temperature for extraction is usually from room temperature to 90° C., preferably 60° C. to 80° C. The weight ratio of the inorganic acid to the oily layer is usually 0.5:1 to 8:1, preferably 3:1 to 6:1. The inorganic acid used as the extracting agent is preferably the same one as used for acidifying the aqueous solution of alkali metal salts of organic acids in the step (i). For example, when sulfuric acid is used to acidify the aqueous solution of alkali metal salts of organic acids in the step (i), it is preferable to also use sulfuric acid to extract the useful organic acids from the oily layer.

After extracting the oily layer with an aqueous solution of a protic inorganic acid, the concentration of sodium ion in the waste oily layer can be reduced to as low as 20 ppm by weight. Therefore, the waste oily layer can be utilized, optionally together with other fuel oils such as a heavy oil, as a fuel for a boiler or a combustion system. In addition, the extraction efficacy can be significantly raised in view that the amount of the useful organic acids extracted by an aqueous solution of a protic inorganic acid is as 1.5 to 1.8 times as that extracted by an aqueous solution of sodium sulfate under the same condition. The aqueous extract comprising the organic acids dissolved in the aqueous solution of the protic inorganic acid obtained from said step (ii) will be further treated in the step (iv).

In the step (iii) of the method according to the present invention, the useful organic acids essentially comprising adipic acid and 6-hydroxycaproic acid, are extracted from the aqueous layer obtained from the step (i) with an organic solvent. The aqueous layer separated from the step (i), which is an aqueous solution of the alkali metal salt of inorganic acid, still contains some useful organic acids that are not completely extracted by the aqueous solution of inorganic acid. The useful organic acids contained in said aqueous layer can be recovered by extraction with the organic solvents. The organic solvents as the extracting agents are selected from ketones, alcohols, esters or the mixtures thereof, wherein the extracting agents of two-solvent type, such as those consisting of cyclohexanol and cyclohexanone in a ratio of 1:4 to 4:1, preferably 3:2, can extract the useful organic acids from the aqueous layer more completely and hence are preferable when compared with the extracting agents of one-solvent type such as methyl isobutyl ketone,. More preferably, the raw products of cyclohexane oxidation is directly used as the extracting agent. The weight ratio of the extracting agent to the aqueous layer obtained from step (i) is usually from 0.5:1 to 3:1.

The oily extract comprising the organic acids obtained from the step (iii) will be further treated in the step (v) to recover the useful organic acids contained therein. In addition, said oily extract comprising the useful organic acids can also be utilized as an extracting agent in the step (iv) to extract the useful organic acids from the aqueous extract obtained from the step (ii).

The residual aqueous layer after extraction in the step (iii), can be concentrated to form the crystals of alkali metal salts of inorganic acids. Owing that the residual aqueous layer has been extracted with the organic solvents previously, it contains less organic impurities and consequently the quality of the crystals obtained therefrom can be improved.

In the step (iv) of the method according to the present invention, the useful organic acids are extracted from the aqueous extract obtained from the step (ii) with organic solvents. The extracting agent used in the step (iv) is selected from the same organic solvents as used in the step (iii), for example, ketones, alcohols, esters or the mixtures thereof. Alternatively and preferably, the oily extract comprising organic acids obtained from the step (iii) is directly used as an extracting agent to extract the useful organic acids from the aqueous extract obtained from the step (ii).

The oily extract comprising the organic acids obtained in said step (iv) will be further treated in the step (v) to recover the useful organic acids. The aqueous extract left after extraction, which comprises the protic inorganic acid, is preferably distilled to recover the residual organic solvents. The residual aqueous extract (hereinafter called a mother liquor comprising the protic inorganic acid ) can be recycled to the step (ii) for use as the extracting agent or recycled to the step (i) as the acidifying agent.

According to the present invention, the COD value (indicating the amount of the organic matters) of the mother liquor comprising the protic inorganic acid is just mildly raised even after said mother liquor has been recycled for many times. Therefore said mother liquor is allowed to be reused repeatedly.

In the step (v) of the method according to the present invention, the oily extracts comprising the organic acids obtained from the step (iii) and the step (iv) are combined and distilled to recover the organic solvents and the useful organic acids essentially comprising adipic acid and 6-hydroxycaproic acid. These useful organic acids will be converted to 1,6-hexanediol according to the conventional methods. The recovered organic solvents are recycled to the step (iii) for reuse.

According to the present invention, a preferred method of recovering adipic acid and 6-hydroxycaproic acid from the waste solution of alkali metal salts of organic acids coming from the process of cyclohexane oxidation, comprises the following steps:

(i) basifying the reaction mixture coming from cyclohexane oxidation with an aqueous solution of an alkalimetal base so that the organic acids essentially comprising adipic acid and 6-hydroxy caproic acid therein are saponified, extracting the formed alkali metal salts of organic acids from the mixture with water, then acidifying the aqueous extract comprising the alkali metal salts of organic acids to a pH value of 3 or lower with an aqueous solution of a protic inorganic acid, as a result, said aqueous extract is separated into an oily layer and an aqueous layer;

(ii) extracting the organic acids from said oily layer obtained from the step(i) with an aqueous solution of a protic inorganic acid, to obtain an aqueous extract;

(iii) extracting the organic acids from said aqueous layer obtained from the step (i), with an organic solvent consisting of alcohols, ketones, esters or the mixtures thereof, to obtain an oily extract;

(iv) extracting the organic acid from the aqueous extract obtained from the step(ii) with the oily extract obtained in the step (iii), to obtain an oily extract ; and (v) distilling the oily extracts obtained from the step (iv), to recover the organic acids essentially comprising adipic acid and 6-hydroxycaproic acid.

In reference to FIG. 1, said preferred method of the present invention is illustrated in more details.

FIG. 1 is a flow chart of recovering adipic acid and 6-hydroxycaproic acid from the waste solution of sodium salts of organic acids coming from the process of cyclohexane oxidation in accordance with a preferred embodiment of the present invention.

The liquid-phase oxidation of cyclohexane is carried out in the presence of a catalyst such as a cobalt salt, at a temperature of 150 to 165° C. and a pressure of 8 to 10 atm. After the reaction is completed, the reaction mixture is basified with an aqueous solution of sodium hydroxide, thereby the organic acids contained therein are saponified. Then, the mixture is extracted with water to obtain an aqueous extract comprising sodium salts of the organic acids (S-1), which essentially comprise adipic acid and 6-hydroxycaproic acid. S-1 is delivered to an acidifying tank (T-1) and acidified there to a pH value of 3 or lower with an aqueous solution of a protic inorganic acid (S-2) such as sulfuric acid, phosphoric acid, nitric acid or hydrochloric acid. As a result, S-1 is separated into an aqueous layer (S-3) and an oily layer (S-4).

The oily layer (S-4), usually containing 0.2 to 0.9% by weight of sodium ion, is delivered to an extracting tower (T-2) and extracted there with an aqueous solution of a protic inorganic acid (S-5) such as sulfuric acid, phosphoric acid, nitric acid or hydrochloric acid. The concentration of said protic inorganic acid in S-5 is usually in a range of 5 to 50% by weight, preferably 15 to 30% by weight. The temperature for extraction is usually from room temperature to 90° C., preferably 60° C. to 80° C. The weight ratio of the inorganic acid to the oily layer (S-4) is 0.5:1 to 8:1, preferably 3:1 to 6:1. In addition, the inorganic acid used here is preferably the same one as used for acidifying the aqueous extract comprising the sodium salts of organic acids (S-1).

After extraction of S-4 with S-5, the waste oily layer (S-6), having a concentration of sodium ion below 20 ppm by weight, is delivered to a mixing tank (T-4) and mixed with a heavy oil (S-7) there, thereby providing a fuel (P-1) for a boiler or combustion system; and the obtained aqueous extract (S-8) comprising the organic acids dissolved in the aqueous solution of the protic inorganic acid, is delivered to an extracting tower (T-7) and treated as described below.

In another aspect, the aqueous layer (S-3) obtained above is delivered to an extracting tower (T-3) and extracted there with organic solvents (S-9), to recover the residual useful organic acids which are not transferred into the oily layer (S-4) after acidification of S-1. The organic solvents as the extracting agents are selected from ketones, alcohols, esters or the mixtures thereof, wherein the extracting agents of two-solvent type, such as those consisting of cyclohexanol and cyclohexanone in a ratio of 1:4 to 4:1, preferably 3:2, are superior to the extracting agents of one-solvent type. More preferably, the raw products of cyclohexane oxidation is directly used as the extracting agent. The weight ratio of the extracting agent to the aqueous layer is from 0.5:1 to 3:1.

After extraction of S-3 with S-9, the residual aqueous layer (S-10) comprising the sodium salt of inorganic acid is first delivered to a stripping tower (T-5) to recover the residual organic solvents (S-11) therein, and then is delivered to a concentrating and crystallizing tank (T-6) to produce the crystals of sodium salts of inorganic acids (P-2). In another aspect, the obtained oily extract (S-12) comprising the organic acids is delivered to the extracting tower (T-7) and used as an extracting agent to extract the aqueous extract (S-8).

The aqueous layer (S-13) left after extraction S-8 with S-12 is first delivered to a stripping tower (T-8) to recover the residual organic solvent (S-14) therein. Then the residual aqueous layer (S-15) after stripping, which is also called "mother liquor comprising the protic inorganic acid", is recycled to the acidifying tower (T-1) to acidify the aqueous extract comprising alkali metal salts of organic acids (S-1) or recycled to the extracting tower (T-2) as the extracting agent.

In another aspect, the oily extract (S-16) comprising the organic acids obtained from extraction S-8 with S-12 is delivered to a distilling tower (T-9) and distilled there to recover the organic solvent (S-17) and the useful organic acids (S-18). The recovered organic solvents (S-17), together with the recovered organic solvents (S-11) and (S-14) are recycled to the extracting tower T-3 for use as the extracting agent; and the useful organic acids, which are mainly adipic acid and 6-hydroxycaproic acid, are converted into 1,6-hexanediol (P-3).

The characteristics and advantages of the present invention will become apparent from the following examples. The present examples are therefore to be considered in all aspects as illustrative but not restrictive. Any change and amendment that is within the spirit and range of the claims can be made by the persons skilled in the art and such change and amendment are therefore intended to be embraced in the present invention.

EXAMPLE 1

The reaction mixture coming from cyclohexane oxidation was basified with an aqueous solution of sodium hydroxide so that the organic acids therein were converted into the salts. Then the mixture was extracted by water to obtain an aqueous extract comprising the sodium salts of the organic acids, which contained 5.18% of adipic acid (calculated as acid) and 5.22% of 6-hydroxycaproic acid (calculated as acid). 9.6 kg of the aqueous extract comprising the sodium salts of the organic acids was acidified to a pH value of 2.8 by adding 4.01 kg of a 37% aqueous solution of sulfuric acid thereto at 65° C. As a result, 3.33 kg of an oily layer comprising the organic acids and 10.28 kg of an aqueous layer comprising sodium sulfate were obtained.

The oily layer comprising the organic acids, containing 0.5% of sodium ion, was then extracted with 16.67 kg of a 18% aqueous solution of sulfuric acid at 70 to 80° C., thereby obtaining 18.34 kg of an aqueous extract comprising the organic acids dissolved in an aqueous solution of sulfuric acid and 1.66 kg of the waste oily layer. The waste oily layer contained as low as 9 ppm of sodium ions.

The aqueous layer comprising sodium sulfate obtained above was extracted by 10.28 kg of a mixture of cyclohexanol and cyclohexanone at room temperature, thereby obtaining 8.87 kg of the residual aqueous layer comprising sodium sulfate and 11.69 kg of an oily extract comprising organic acids. This oily extract comprising organic acids was used to extract the organic acids from the previously obtained aqueous extract comprising the organic acids dissolved in an aqueous solution of sulfuric acid. The obtained oily extract was distilled to recover the organic solvents and obtain 356 g of adipic acid and 189 g of 6-hydroxycaproic acid (total yield: 54.7%). The aqueous extract left after extraction was distilled to recover the residual organic solvents and the residual aqueous extract (i.e. the mother liquor comprising sulfuric acid) was recycled for use as the acidifying agent and the extracting agent.

EXAMPLE 2

An oily layer comprising the organic acids (3.33 kg) and an aqueous layer comprising sodium sulfate (10.28 kg) were obtained after acidification of the aqueous extract of sodium salts of the organic acids in the same manner as in Example 1.

3.33 kg of the oily layer comprising the organic acids was then extracted with 16.67 kg of a 18% aqueous solution of phosphoric acid at 70 to 80° C., thereby obtaining 18.37 kg of an aqueous extract comprising the organic acids dissolved in the aqueous solution of phosphoric acid and 1.63 kg of the waste oily layer. The waste oily layer contained as low as 11 ppm of sodium ion.

10.28 kg of the aqueous layer comprising sodium sulfate was extracted by 10.28 kg of a mixture of cyclohexanol and cyclohexanone at room temperature, thereby obtaining 8.87 kg of the residual aqueous layer comprising sodium sulfate and 11.69 kg of an oily extract comprising organic acids. This oily extract comprising organic acids was used to extract the organic acids from the aqueous extract comprising the organic acids dissolved in the aqueous solution of phosphoric acid, and the obtained oily extract is distilled to recover the useful organic acids and the organic solvents. Finally, 327 g of adipic acid and 178 g of 6-hydroxycaproic acid were obtained, and the total yield was 51.9%.

EXAMPLE 3

The aqueous layer comprising sodium sulfate obtained after acidification of the aqueous solution of sodium salts of organic acids in Example 1 had a COD value of 6.60%, but said COD value was lowered to 1.77% after extraction with the organic solvent. Therefore, the crystals of anhydrous sodium sulfate produced therefrom had a low COD value.

The mother liquor comprising sulfuric acid obtained in Example 1 also had a low COD value. Even when said mother liquor was used repeatedly, the COD values of both the mother liquor and the sodium sulfate crystals were only mildly raised.

Figure 2:
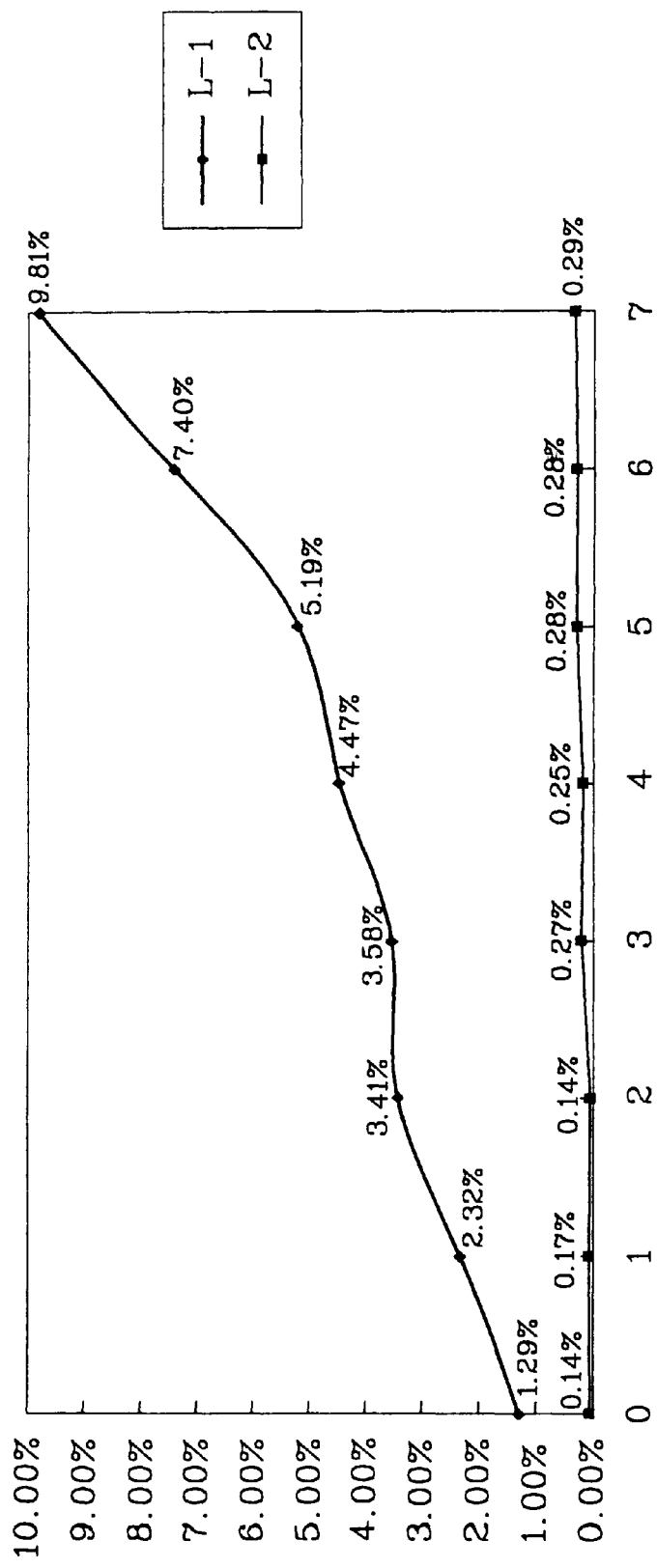
FIG. 2 is a graph of COD values of sodium sulfate crystals versus the recycle numbers of sulfuric acid-containing mother liquor, wherein L-1 represents the curve referring to the sodium sulfate crystals obtained from Comparative Example 2, and L-2 represents the curve referring to the sodium sulfate crystals obtained from Example 1.
Figure 3:
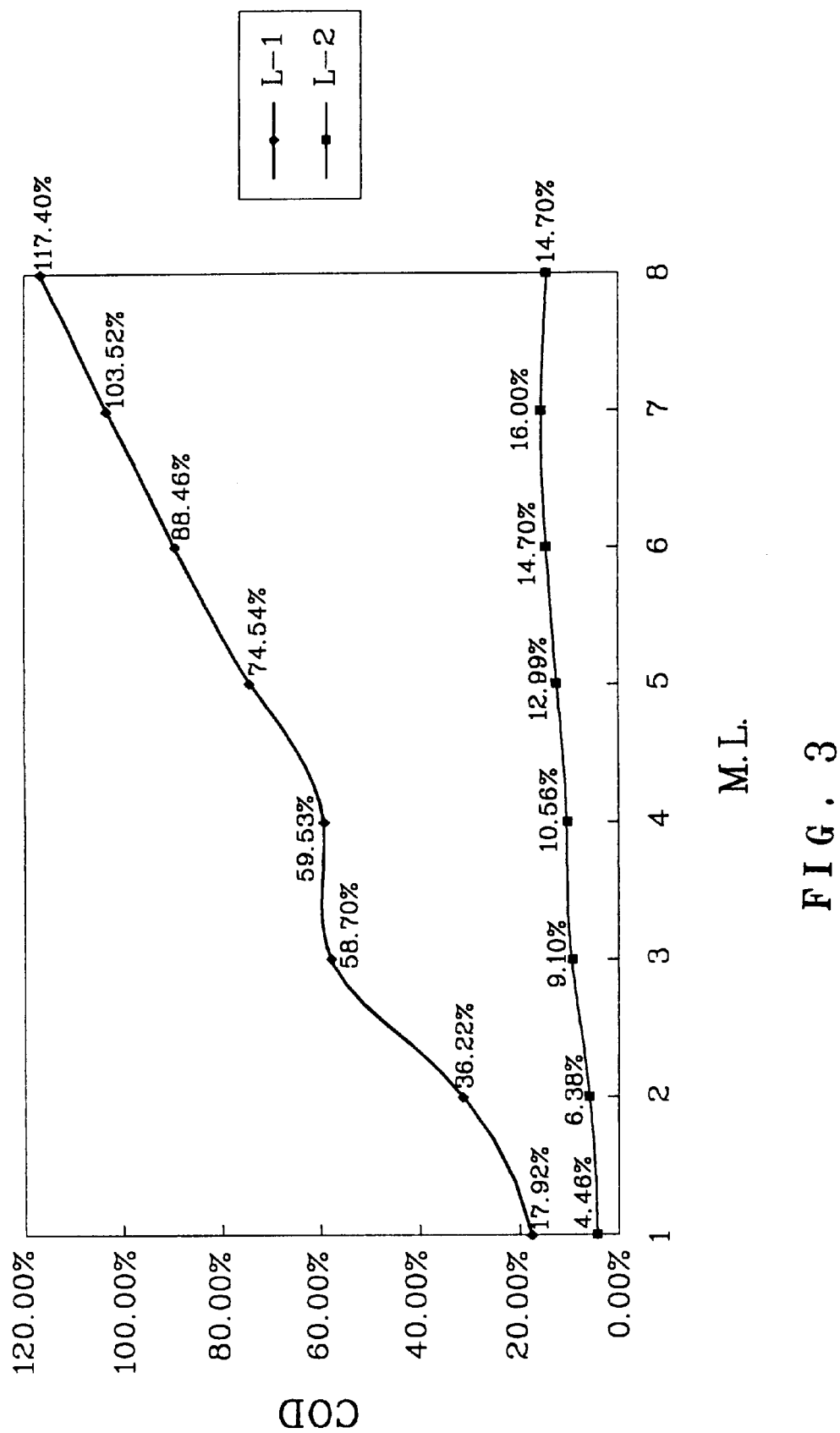
FIG. 3 is a graph of COD values of the mother liquor versus the recycle numbers of the mother liquor, wherein L-1 represents the curve referring to the sodium sulfate-containing mother liquor in Comparative Example 2, and L-2 represents the curve referring to the sulfuric acid-containing mother liquor in Example 1.

As shown in FIG. 2, the COD value of the sodium sulfate crystals was 0.14% at the first run and was merely raised to 0.29% after the mother liquor has been recycled for 7 times (referring to the curve L-2). Also as shown in FIG. 3, the initial COD value of the mother liquor was 4.46% and was raised to 14.70% after said mother liquor has been recycled for 7 times (referring to the curve L-2).

COMPARATIVE EXAMPLE 1

An oily layer comprising the organic acids (3.33 kg) and an aqueous layer comprising sodium sulfate (10.28 kg), were obtained in the same manner as in Example 1.

3.33 kg of said oily layer comprising the organic acids was extracted at 70 to 80 ° C. with 16.67 kg of a 18% aqueous solution of sodium sulfate, thereby obtaining 17.67 kg of an aqueous extract comprising the organic acids dissolved in the aqueous solution of sodium sulfate and 2.33 kg of the waste oily layer. The waste oily layer contained as high as 0.25% of sodium ion.

10.28 kg of said aqueous layer comprising sodium sulfate was extracted by 10.28 kg of a mixture of cyclohexanol and cyclohexanone at room temperature, thereby obtaining 8.87 kg of the residual aqueous layer comprising sodium sulfate and 11.69 kg of an oily extract comprising organic acids. This oily extract comprising organic acids was used to extract the previously obtained aqueous extract comprising the organic acids dissolved in the aqueous solution of sodium sulfate. The obtained oily extract was distilled to recover the organic solvents and obtain 272 g of adipic acid and 116 g of 6-hydroxycaproic acid (total yield: 39.0%).

COMPARATIVE EXAMPLE 2

The aqueous layer comprising sodium sulfate obtained after acidification of the aqueous solution of sodium salts of organic acids in Example 1 had a COD value of 6.60%. When said aqueous layer comprising sodium sulfate was not extracted with the organic solvents but was directly concentrated to form the crystals of anhydrous sodium sulfate or recycled for use as the extracting agent, then the COD values of the sodium sulfate crystals and the recycled mother liquor increased rapidly.

As shown in FIG. 2, the COD value of the sodium sulfate crystals was 1.29% at the first run and was raised to 9.81% after the mother liquor has been recycled for 7 times (referring to the curve L-1). Also as shown in FIG. 3, the initial COD value of the mother liquor comprising sodium sulfate was 17.92% at the first run and was raised to 117.40% after the mother liquor has been recycled for 7 times (referring to the curve L-1).

We claim:

1. A method of recovering adipic acid and 6-hydroxycaproic acid from the waste solution of alkali metal salts of organic acids coming from the process of cyclohexane oxidation, comprising the following steps:

(i) basifying the reaction mixture coming from cyclohexane oxidation with an aqueous solution of an alkali-metal base so that the organic acids essentially comprising adipic acid and 6-hydroxycaproic acid therein, are saponified, extracting the formed alkali metal salts of organic acids from the mixture with water, then acidifying the aqueous extract comprising the alkali metal salts of organic acids to a pH value of 3 or lower with an aqueous solution of a protic inorganic acid, as a result, said aqueous extract is separated into an oily layer and an aqueous layer;

(ii) extracting the organic acid from said oily layer obtained from the step (i) with an aqueous solution of a protic inorganic acid, to obtain an aqueous extract;

(iii) extracting the organic acid from the aqueous layer obtained from the step (i) with an organic solvent selected from alcohols, ketones, esters or the mixtures thereof, to obtain an oily extract;

(iv) extracting the organic acid from the aqueous extract obtained from the step (ii) with an organic solvent selected from alcohols, ketones, esters or mixtures thereof, to obtain an oily extract; and (v) combining and distilling the oily extracts obtained from the steps (iii) and (iv), to recover the organic acid essentially comprising adipic acid and 6-hydroxycaproic acid.

2. The method according to claim 1, wherein the aqueous solution of a protic inorganic acid used as the extracting agent in the step (ii) is the same one as used in the step (i) for acidifying the aqueous extract comprising the alkali metal salts of organic acids.

3. The method according to claim 1, wherein the aqueous extract obtained from the step (ii) after extraction with an organic solvent selected from alcohols, ketones, esters or mixtures thereof in the step (iv), can be recycled to the step (ii) as the extracting agent or recycled to the step (i) to acidify the aqueous extract comprising the alkali metal salts of organic acids.

4. The method according to any one of claims 1 to 3, wherein the protic inorganic acid is selected from sulfuric acid, phosphoric acid, nitric acid or hydrochloric acid.

5. The method according to any one of claims 1 to 3, wherein the concentration of the protic inorganic acid in the aqueous solution is 5 to 50% by weight.

6. The method according to claim 5, wherein the concentration of the protic inorganic acid in the aqueous solution is 15 to 30% by weight.

7. The method according to claim 1, wherein in the step (ii), the oily layer is extracted with the aqueous solution of protic inorganic acid at a temperature from room temperature to 90° C. and the weight ratio of the aqueous solution of protic inorganic acid to the oily layer is 0.5:1 to 8:1.

8. The method according to claim 7, wherein in the step (ii), the oily layer is extracted with the aqueous solution of protic inorganic acid at a temperature from 60° C. to 80° C., and the weight ratio of the aqueous solution of protic inorganic acid to the oily layer is 3:1 to 6:1.

9. The method according to claim 1, wherein the organic solvent used as the extracting agent in the step (iii) is a mixture of cyclohexanol and cyclohexanone in a ratio 1:4 to 4:1.

10. The method according to claim 9, wherein the mixture of cyclohexanol and cyclohexanone is the raw product coming from the process of cyclohexane oxidation.

11. The method according to claim 9, wherein the ratio of cyclohexanol to cyclohexanone is 3:2.

12. The method according to claim 1, wherein the ratio of the organic solvent to the aqueous layer in the step (iii) is 0.5:1 to 3:1.

13. The method according to claim 1, wherein in the step (ii), after the oily layer obtained in the step (i) has been extracted with an aqueous solution of a protic inorganic acid, the waste oily layer left can be utilized, together with a heavy oil, as a fuel for a boiler or a combustion system.

14. The method according to claim 1, wherein in the step (iii), after the aqueous layer obtained from the step (i) has been extracted with an organic solvent, the residual aqueous layer is concentrated to form the crystals of alkali metal salts of inorganic acid.

15. A method of recovering adipic acid and 6-hydroxycaproic acid from the waste solution of alkali metal salts of organic acids coming from the process of cyclohexane oxidation, comprising the following steps:

(i) basifying the reaction mixture coming from cyclohexane oxidation with an aqueous solution of an alkali-metal base so that the organic acids essentially comprising adipic acid and 6-hydroxy caproic acid therein are saponified, extracting the formed alkali metal salts of organic acids from the mixture with water, then acidifying the aqueous extract comprising the alkali metal salts of organic acids to a pH value of 3 or lower with an aqueous solution of a protic inorganic acid, as a result, said aqueous extract is separated into an oily layer and an aqueous layer;

(ii) extracting the organic acids from said oily layer obtained from the step (i) with an aqueous solution of a protic inorganic acid, to obtain an aqueous extract;

(iii) extracting the organic acids from the aqueous layer obtained from the step (i), with an organic solvent consisting of alcohols, ketones, esters or the mixtures thereof, to obtain an oily extract;

(iv) extracting the organic acids from the aqueous extract obtained from the step (ii) with the oily extract obtained in the step (iii), to obtain an oily extract; and (v) distilling the oily extracts obtained from the step (iv), to recover the organic acids essentially comprising adipic acid and 6-hydroxycaproic acid.

* * * * *

UNITED STATES PATENT AND TRADEMARK OFFICE
CERTIFICATE OF CORRECTION

PATENT NO. : 6,063,958
DATED : May 16, 2000
INVENTOR(S) : Kuang-Ruei Chen; Jih-Dar Hwang; Shu-Hui Chen It is certified that error appears in the above-indentified patent and that said Letters Patent is hereby corrected as shown below:

In column 1, line 32, please change "esternfication" to --esterification--.

Signed and Sealed this

Twenty-seventh Day of March, 2001

Attest:

NICHOLAS P. GODICI

Attesting Officer *Acting Director of the United States Patent and Trademark Office*